United States Patent [19]

Peters

[11] 4,380,635
[45] Apr. 19, 1983

[54] SYNTHESIS OF ACYLATED BENZOTHIOPHENES

[75] Inventor: Mary K. Peters, Indianapolis, Ind.

[73] Assignee: Eli Lilly and Company, Indianapolis, Ind.

[21] Appl. No.: 331,046

[22] Filed: Dec. 16, 1981

Related U.S. Application Data

[63] Continuation-in-part of Ser. No. 246,333, Apr. 3, 1981, abandoned.

[51] Int. Cl.$^3$ ............................................. C07D 333/64
[52] U.S. Cl. ................................. 546/202; 260/330.3; 544/146; 548/525; 549/51
[58] Field of Search ................... 260/326.5 SA, 330.3; 544/146; 546/202; 549/51

[56] References Cited

U.S. PATENT DOCUMENTS

| | | | |
|---|---|---|---|
| 3,947,470 | 3/1976 | Brenner et al. | 260/330.5 |
| 3,983,245 | 9/1976 | Ladd et al. | 424/285 |
| 4,001,426 | 1/1977 | Brenner et al. | 424/285 |
| 4,133,814 | 1/1979 | Jones et al. | 260/326.55 |

OTHER PUBLICATIONS

Ong, Tetrahedron Letters, vol. 21, (1980), pp. 4225–4228.
Node et al., J. Org. Chem., vol. 46, No. 10, (1981), pp. 1991–1993.
Fuji et al., J. Org. Chem., vol. 44, (1979), pp. 1661–1664.
Node et al., J. Chem. Soc., Perkin I, (1976), pp. 2237–2240.
Fuji et al., Chem. Pharm. Bul., vol. 28, (1980), pp. 3662–3664.
Williard et al., Tet. Let., vol. 21, (1980), pp. 3731–3734.
Hanessian et al., Tet. Let., vol. 21, (1980), pp. 2305–2308.
Kiso et al., Chem. Pharm. Bul., vol. 28, (1980), pp. 673–676.
Kiso, J. Chem. Com., (1979), pp. 971 and 972.
Irie et al., Chem. Pharm. Bul., vol. 25, (1977), pp. 2929–2934.
Fujita et al., Tetrahedron Letters No. 52, 5211–5214, (1978).
Chemistry Letters, 97–98, (1979).
J. Org. Chem., 45, 4275–4277, (1980).
Node et al., Tet. Let., 23, 689–692, (1982).

Primary Examiner—Richard Raymond
Attorney, Agent, or Firm—Joseph A. Jones; Arthur R. Whale

[57] ABSTRACT

A group of 6-hydroxy-2-(4-hydroxyphenyl)-3-[4-(2-aminoethoxy)benzoyl]benzo[b]thiophenes are prepared by acylation of a methyl-protected starting compound followed by demethylation in a single reaction mixture.

13 Claims, No Drawings

SYNTHESIS OF ACYLATED BENZOTHIOPHENES

CROSS-REFERENCE

This application is a continuation-in-part of copending application Ser. No. 246,333, filed Apr. 3, 1981, now abandoned.

BACKGROUND OF THE INVENTION

1. Field of the Invention

This invention belongs to the field of pharmaceutical chemistry, and provides an advantageous process for preparing a group of 6-hydroxy-2-(4-hydroxyphenyl)-3-[4-(2-aminoethoxy)benzoyl]benzo[b]thiophenes. The process uses methyl groups to protect the hydroxy groups during the synthesis, and provides the compounds in excellent yield without isolating the intermediate product.

2. State of the Art

U.S. Pat. No. 4,133,814, of Jones and Suarez, first taught most of the compounds which are prepared by the process of this invention, and showed a number of processes for preparing them. The patent shows the use of phenacyl, halophenacyl and alkyl protecting groups. The process does not, however, suggest the particularly advantageous way to use a methyl protecting group which is provided by this invention.

Fujita et al. have shown the use of aluminum halide-thiols as a reagent for the demethylation of various aliphatic and aromatic ethers. The compounds on which they worked, however, were of a very stable nature, and it is believed that Fujita's work suggests that aluminum halide-thiol could not be applied to the complex polyfunctional molecules with which this invention is concerned. Fujita's work was published in *Chemistry Letters*, 97–98 (1979), *Tet. Let.*, 5211–14 (1978), and *J. Org. Chem.* 45, 4275–77 (1980).

SUMMARY OF THE INVENTION

This invention provides a process for preparing a compound of the formula

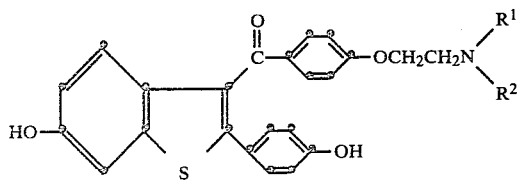

wherein $R^1$ and $R^2$ are independently $C_1$–$C_4$ alkyl, or combine to form $C_4$–$C_6$ polymethylene, —$CH_2CH(CH_3)CH_2CH_2$—, or —$(CH_2)_2O(CH_2)_2$—; which process comprises acylating a compound of the formula

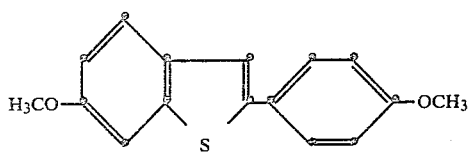

in the presence of aluminum chloride or aluminum bromide with an acylating agent of the formula

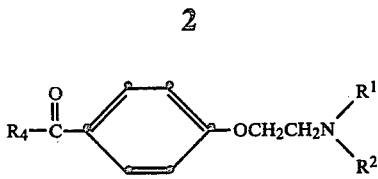

wherein $R^4$ is chloro or bromo; and adding to the reaction mixture a sulfur compound chosen from the group consisting of methionine and compounds of the formula

X—S—Y wherein X is hydrogen or unbranched $C_1$–$C_4$ alkyl, and Y is $C_1$–$C_4$ alkyl or phenyl.

DESCRIPTION OF THE PREFERRED EMBODIMENTS

In this document, all temperatures are stated in degrees Celsius. All amounts, ratios, concentrations, proportions and the like are stated in weight units unless otherwise stated, except for ratios of solvents which are in volume units.

In the general formula above, the general terms bear their usual meanings. For example, the term $C_1$–$C_4$ alkyl refers to groups such as methyl, ethyl, propyl, s-butyl, t-butyl and the like. The term $C_4$–$C_6$ polymethylene refers to tetramethylene, pentamethylene and hexamethylene. The term unbranched $C_1$–$C_4$ alkyl refers to methyl, ethyl, propyl and butyl.

This invention provides a convenient process which acylates the methyl-protected starting compound, and then demethylates it to obtain the desired dihydroxy product. The acylation and demethylation are performed in successive steps in a single reaction mixture.

The following group of representative products of the process of this invention will be mentioned, to assure that the reader fully understands the purpose of the process.

6-hydroxy-2-(4-hydroxyphenyl)-3-[4-(2-dimethylaminoethoxy)benzoyl]benzo[b]thiophene
3-[4-(2-ethylmethylaminoethoxy)benzoyl]-6-hydroxy-2-(4-hydroxyphenyl)benzo[b]thiophene
3-[4-(2-ethylisopropylaminoethoxy)benzoyl]-6-hydroxy-2-(4-hydroxyphenyl)benzo[b]thiophene
3-[4-(2-dibutylaminoethoxy)benzoyl]-6-hydroxy-2-(4-hydroxyphenyl)benzo[b]thiophene
3-[4-[2-(1-methylpropyl)methylaminoethoxy]-benzoyl]-6-hydroxy-2-(4-hydroxyphenyl)benzo[b]thiophene
6-hydroxy-2-(4-hydroxyphenyl)-3-[4-[2-(3-methylpyrrolidino)ethoxy]benzoyl]benzo[b]thiophene
6-hydroxy-2-(4-hydroxyphenyl)-3-[4-[2-di(2-methylpropyl)aminoethoxy]benzoyl]benzo[b]thiophene
6-hydroxy-2-(4-hydroxyphenyl)-3-[4-(2-pyrrolidinoethoxy)benzoyl]benzo[b]thiophene
6-hydroxy-2-(4-hydroxyphenyl)-3-[4-(2-piperidinoethoxy)benzoyl]benzo[b]thiophene
6-hydroxy-2-(4-hydroxyphenyl)-3-[4-(2-morpholinoethoxy)benzoyl]benzo[b]thiophene
3-[4-(2-hexamethyleneiminoethoxy)benzoyl]-6-hydroxy-2-(4-hydroxyphenyl)benzo[b]thiophene The preferred products of this process are those wherein $R^1$ and $R^2$ combine to form tetramethylene, pentamethylene or —$CH_2CH(CH_3)CH_2CH_2$—.

The methyl-protected starting compound is most easily obtained by a synthesis which is exemplified below in Preparation 1. The process is carried out by reacting 3-methoxybenzenethiol and α-bromo-4- methoxyacetophenone in the presence of a strong base at a relatively low temperature, to form α-(3-methoxyphenylthio)-4-methoxyacetophenone, which is then ring-closed with an agent such as polyphosphoric acid at a high temperature to obtain the desired starting compound.

The acylation of this invention is a Friedel-Crafts acylation, and is carried out in the usual way, using aluminum chloride or bromide, preferably the chloride, as the acylation catalyst.

The acylation is ordinarily carried out in a solvent, and any inert organic solvent which is not significantly attacked by the conditions may be used. For example, halogenated solvents such as dichloromethane, 1,2-dichloroethane, chloroform and the like may be used, as can aromatics such as benzene, chlorobenzene and the like. It is preferred to use a halogenated solvent, especially dichloromethane.

It has been found that toluene is rather easily acylated under the conditions used in the Friedel-Crafts acylation step, and so it is important, when toluene is used in an earlier step of the process, to remove it as completely as possible from the protected starting compound, to avoid wasting the acylating agent.

The acylations may be carried out at temperatures from about $-30°$ to about $100°$, preferably at about ambient temperature, in the range of about $15°$ to about $30°$.

The acylating agent is an active form of the appropriate benzoic acid, wherein $R^4$ is a chlorine or bromine atom.

The preferred acylating agents are those wherein $R^4$ is chloro. Thus, the most highly preferred individual acylating agents are 4-(2-piperidinoethoxy)benzoyl chloride, 4-[2-(3-methylpyrrolidino)ethoxy]benzoyl chloride and 4-(2-pyrrolidinoethoxy)benzoyl chloride.

The examples below show clearly that the acyl chloride used as an acylating agent may be prepared from the corresponding carboxylic acid by reaction with a typical chlorinating agent such as thionyl chloride. Care must be taken to remove any excess chlorinating agent from the acyl chloride, however. Most conveniently, the acyl chloride is formed in situ, and the excess chlorinating agent is distilled off under vacuum.

The stoichiometric amounts of the benzothiophene and the acylating agent may be used effectively. If desired, a small excess of either reactant may be added to assure that the other is fully consumed.

It is preferred to use a large excess of the acylation catalyst, such as about 2-12 moles per mole of product, preferably about 5-10 moles.

The acylation is rapid. Economically brief reaction times such as from about 15 minutes to a few hours provide high yields of the acylated intermediate. Longer reaction times may be used if desired but are not usually advantageous. As usual, the use of lower reaction temperatures calls for relatively long times.

The acylation step is ended, and the demethylation step begun, by adding the sulfur compound to the reaction mixture.

The sulfur compounds are, preferably, the alkylthiols, such as methanethiol, ethanethiol, the preferred agent, isopropanethiol, butanethiol and the like; dialkyl sulfides, such as diethyl sulfide, butyl s-butyl sulfide, ethyl propyl sulfide, butyl isopropyl sulfide, dimethyl sulfide, methyl ethyl sulfide and the like; benzenethiol; methionine; and alkyl phenyl sulfides such as methyl phenyl sulfide, ethyl phenyl sulfide, butyl phenyl sulfide and the like.

It has been found that the demethylation goes best when a substantial excess amount of the sulfur compound is used, in the range of from about 4 to about 10 moles per mole of the starting benzothiophene. The process can be carried out, although less efficiently, with a smaller amount of the sulfur compound in the range of about 2 or 3 moles per mole of starting compound. It is also possible to use a small amount of the sulfur compound, such as 2 or 3 moles per mole of starting compound, and to improve the yield by the addition of about 1 to 3 moles of an alkali metal halide, such as sodium, potassium or lithium chloride, iodide or bromide. (A similar effect of sodium iodide is shown by Niwa et al., *Tet. Let.* 22, 4239-40 (1981)).

The demethylation reaction goes well at about ambient temperature, in the range of from about $15°$ to about $30°$, and such operation is preferred. However, the demethylation step may be carried out at temperatures in the range of from about $-30°$ to about $50°$ if it is desired to do so. Short reaction times in the range of about 1 hour have been found to be adequate.

After the product has been demethylated, it is recovered and isolated by conventional means. It is customary to add water to decompose the complex of the acylation catalyst; addition of dilute aqueous acid is advantageous. The product precipitates in many instances, or may be extracted with an organic solvent according to conventional methods. The examples below further illustrate the isolation.

The products of this process may be recovered as the free bases, or as acid addition salts as is conventional in the synthesis of amine-containing products. For example, the compounds may be isolated as salts of inorganic or organic acids such as hydrobromic acid, hydriodic acid, sulfonic acids including such agents as naphthalenesulfonic, methanesulfonic and toluenesulfonic acids, sulfuric acid, nitric acid, phosphoric acid, tartaric acid, pyrosulfuric acid, metaphosphoric acid, succinic acid, formic acid, phthalic acid, lactic acid and the like, preferably with hydrochloric acid, citric acid, benzoic acid, maleic acid, acetic acid or propionic acid. For example, the product may be isolated as the hydrochloride simply by using dilute hydrochloric acid to decompose the catalyst complex.

The following preparation and examples further illustrate the manner in which this invention is carried out. The first preparation below shows an advantageous synthesis of the dimethoxy starting compound.

PREPARATION 1

6-methoxy-2-(4-methoxyphenyl)benzo[b]thiophene

A 100 g. portion of 3-methoxybenzenethiol and 39.1 g. of potassium hydroxide dissolved in 300 ml. of water were added to 750 ml. of denatured ethanol, and the flask was put in a cooling bath. A total of 164 g. of α-bromo-4-methoxyacetophenone was then added in small portions, and the mixture was stirred for 10 minutes in the cooling bath after the addition was complete and then for 3 hours at ambient temperature. The solvent was then evaporated off in vacuum, and 200 ml. of water was added. The mixture was extracted with ethyl acetate, and the organic layer was washed twice with water, twice with aqueous sodium bicarbonate solution, and twice with aqueous sodium chloride solution. The organic layer was then dried over magnesium sulfate, filtered and evaporated under vacuum to obtain 202 g. of crude α-(3-methoxyphenylthio)-4-methoxyacetophenone, which was recrystallized from methanol and washed with hexane to obtain 158 g. of purified product, m.p. 53° C.

A 124 g. portion of the above intermediate was added in small portions to 930 g. of polyphosphoric acid at 85° C. The temperature rose to 95° C. during the addition, and the mixture was stirred at 90° C. for 30 minutes after the addition was complete, and was then stirred an additional 45 minutes while it cooled without external heating. One liter of crushed ice was then added to the mixture, and an external ice bath was applied to control the temperature while the ice melted and diluted the acid. Five hundred ml. of additional water was added, and the light pink precipitate was filtered off and washed, first with water and then with methanol. The solids were dried under vacuum at 40° C. to obtain 119 g. of crude 6-methoxy-2-(4-methoxyphenyl)benzo[b]thiophene. The crude product was slurried in hot methanol, filtered, and washed with cold methanol, and the solids were recrystallized from 4 liters of ethyl acetate, filtered, washed with hexane and dried to obtain 68 g. of the desired intermediate product, m.p. 187°–190.5° C.

The following examples illustrate various embodiments of the process of this invention.

EXAMPLE 1

6-hydroxy-2-(4-hydroxyphenyl)-3-[4-(2-piperidinoethoxy)benzoyl]benzo[b]thiophene, hydrochloride Under a nitrogen blanket, a mixture of 2 g. of 4-(2-piperidinoethoxy)benzoic acid, hydrochloride, 2 drops of dimethylformamide, 2.5 ml. of thionyl chloride and 40 ml. of chlorobenzene was heated at 70°–75° C. for about one hour. The excess thionyl chloride and 15–20 ml. of solvent were then distilled off. The remaining suspension was cooled to ambient temperature, and to it were added 100 ml. of dichloromethane, 2.7 g. of 6-methoxy-2-(4-methoxyphenyl)benzo[b]thiophene and 10 g. of aluminum chloride. The solution was stirred for about one hour, 7.5 ml. of ethanethiol was added, and the mixture was stirred for 45 minutes more. Then 40 ml. of tetrahydrofuran was added, followed by 15 ml. of 20% hydrochloric acid, with an exotherm to reflux. Fifty ml. of water and 25 ml. of saturated aqueous sodium chloride were added. The mixture was stirred and allowed to cool to ambient temperature. The precipitate was collected by filtration and washed successively with 30 ml. of water, 40 ml. of 25% aqueous tetrahydrofuran, and 35 ml. of water. The solids were then dried at 40° under vacuum to obtain 5.05 g. of crude product, which was identified by its nmr spectrum, using a 90 mHz instrument and deuterochloroform. δ1.7 (6H, m, N(CH$_2$CH$_2$)$_2$CH$_2$); 2.6–3.1 (2H, m, NCH$_2$); 3.5–4.1 (4H, m, NCH$_2$); 4.4 (2H, m, OCH$_2$); 6.6–7.4 (9H, m, aromatic); 7.7(2H, d, aromatic o to CO); 9.8 (2H, m, OH).

EXAMPLE 2

6-hydroxy-2-(4-hydroxyphenyl)-3-[4-(2-piperidinoethoxy)benzoyl]benzo[b]thiophene, hydrochloride The acid chloride was made from 1.5 g. of 4-(2-piperidinoethoxy)benzoic acid, hydrochloride, as described in Example 1. To the acid chloride were added 30 ml. of dichloromethane, 1.35 g. of 6-methoxy-2-(4-methoxyphenyl)benzo[b]thiophene and 5 g. of aluminum chloride. The mixture was stirred at ambient temperature for 2.5 hours, and then 0.74 g. of lithium iodide was added. The mixture was stirred for 1 hour, and then 0.68 g. of ethanethiol was added and the mixture was stirred for 30 minutes more at a temperature between 25° and 35°. The reaction was then worked up by the addition of 25 ml. of tetrahydrofuran, 5 ml. of 20% hydrochloric acid and 50 ml. of water. The mixture was stirred overnight and was filtered. The solids were washed with 45 ml. of water and then with 40 ml. of diethyl ether, and the product was vacuum dried. The yield was 2.18 g. of product, which was found by 90 mHz nmr analysis to be substantially identical to the product of Example 1.

EXAMPLE 3

6-hydroxy-2-(4-hydroxyphenyl)-3-[4-(2-piperidinoethoxy)benzoyl]benzo[b]thiophene, hydrochloride The process of this example was carried out substantially according to the process of Example 2, except that 0.95 g. of lithium bromide was used instead of lithium iodide. The mixture was worked up as described in Example 2 to obtain 2.6 g. of product, substantially identical to the product of Example 1 by 90 mHz nmr analysis.

EXAMPLE 4

6-hydroxy-2-(4-hydroxyphenyl)-3-[4-(2-piperidinoethoxy)benzoyl]benzo[b]thiophene, hydrochloride The process was run according to the process of Example 2 above, through the addition of aluminum chloride. The mixture was then stirred for 1.5 hours, and 0.81 ml. of ethanethiol was added and the mixture was stirred for 1.5 hours more. A thin layer chromatogram of the mixture indicated that most of the dimethyl intermediate was still present. An additional 0.81 ml. portion of ethanethiol was added, and after the mixture had stirred for 1 hour, 25 ml. of dry tetrahydrofuran was added, followed by 5 ml. of 20% hydrochloric acid and 25 ml. of water. The product was isolated and washed as described above in Example 2 to obtain 2.70 g. of crude product, which was identified by thin layer chromatography as substantially identical to the product of Example 1.

EXAMPLE 5

6-hydroxy-2-(4-hydroxyphenyl)-3-[4-(2-piperidinoethoxy)benzoyl]benzo[b]thiophene, hydrochloride The process of Example 2 was followed again, through the addition of aluminum chloride. The mixture was stirred for 1.5 hours, and to it was then added 1.13 g. of sodium bromide and 0.81 ml. of ethanethiol. The mixture was stirred for 1.25 hours, and it was then quenched by the addition of tetrahydrofuran, hydrochloric acid and water as described in Example 2. Filtration and washing as described in Example 2 produced 2.5 g. of crude dried product, substantially identical to the product of Example 1 according to thin layer chromatography.

EXAMPLE 6

6-hydroxy-2-(4-hydroxyphenyl)-3-[4-(2-piperidinoethoxy)benzoyl]benzo[b]thiophene, hydrochloride The process of this example was carried out according to the process of Example 5 immediately above, except that 0.64 g. of sodium chloride was used in place of sodium bromide. The mixture was worked up as described in the examples immediately above to obtain 2.16 g. of crude product, identical to the product of Example 1 by thin layer chromatography.

EXAMPLE 7

6-hydroxy-2-(4-hydroxyphenyl)-3-[4-(2-pyrrolidinoethoxy)benzoyl]benzo[b]thiophene, hydrochloride The acid chloride was made from 2.85 g. of 4-(2-pyrrolidinoethoxy)benzoic acid, hydrochloride, as described in Example 1. The excess thionyl chloride and most of the solvent were distilled off, and to the residue at ambient temperature were added 80 ml. of dichloromethane, 2.7 g. of 6-methoxy-2-(4-methoxyphenyl)benzo[b]thiophene and 10 g. of aluminum chloride. The mixture was stirred for 45 minutes, 7.5 ml. of ethanethiol was added, and the mixture was stirred for 45 minutes more. To it were then added 5 ml. of methanol, 35 ml. of tetrahydrofuran, 20 ml. of 20% hydrochloric acid, 40 ml. of water and 50 ml. of diethyl ether. A precipitate formed, and was collected by filtration, washed with water and diethyl ether, and dried under vacuum at 80° to obtain 4.36 g. of the desired product in crude form.

One gram of the product was dissolved in 10 ml. of hot methanol and filtered, and the filtrate was concentrated to 5 ml. Ten ml. of diethyl ether was slowly added to it with cooling. The resulting crystals were collected by filtration, washed with diethyl ether and dried at 100° under vacuum to obtain 0.9 g. of purified product, m.p. 226°–227°, which was identified by 90 mHz nmr analysis in DMSO-$d_6$: $\delta$1.9 (m, 4H, N($CH_2CH_2$)$_2$); 3.0–3.7 (m, 6H, $CH_2$N($CH_2CH_2$)$_2$); 4.3–4.5 (m, 2H, O$CH_2CH_2$); 6.6–7.8 (m, 11H, aromatic); 9.87–9.88 (m, 2H, OH).

EXAMPLE 8

6-hydroxy-2-(4-hydroxyphenyl)-3-[4-(2-piperidinoethoxy)benzoyl]benzo[b]thiophene, hydrochloride A 1.5 g. portion of 4-(2-piperidinoethoxy)benzoic acid, hydrochloride, was converted to the acid chloride as described in Example 1, excess volatiles were removed under vacuum, and to the chloride at ambient temperature were added 1.35 g. of 6-methoxy-2-(4-methoxyphenyl)benzo[b]thiophene, 30 ml. of dichloromethane and 5 g. of aluminum chloride. The mixture was stirred for 90 minutes, and to it was added 3.1 g. of dimethyl sulfide. After 20 minutes of stirring, the mixture was cooled to 10°, and 25 ml. of tetrahydrofuran was added to it. It was then warmed to 25°–30°, and 5 ml. of 20% hydrochloric acid and 25 ml. of water were added. The mixture was then heated to 35°, cooled, and stirred overnight. It was then filtered, and the solids were washed on the filter with 60 ml. of water and 30 ml. of diethyl ether. The product was dried under vacuum to obtain 2.65 g. of rather impure product, m.p. 204° dec., which was identified by nmr and thin layer chromatography as substantially identical to the product of Example 1.

EXAMPLE 9

6-hydroxy-2-(4-hydroxyphenyl)-3-[4-(2-piperidinoethoxy)benzoyl]benzo[b]thiophene, hydrochloride The process of this example was the same as that of Example 8, except that the amount of dimethyl sulfide was only 1.6 ml., and the mixture was stirred at ambient temperature for 75 minutes after the addition of the dimethyl sulfide. The reaction mixture was worked up as described in Example 8 to obtain 2.54 g. of the desired crude product, m.p. 207° dec., which was substantially identical to the product of Example 1 by nmr and thin layer chromatography.

EXAMPLE 10

6-hydroxy-2-(4-hydroxyphenyl)-3-[4-(2-piperidinoethoxy)benzoyl]benzo[b]thiophene, hydrochloride The process of Example 8 was repeated again, except that 7.5 g. of methionine was used in place of the dimethyl sulfide, and the reaction mixture was stirred for 45 minutes after the methionine was added, before the work up procedure was begun by the addition of 20 ml. of tetrahydrofuran, 5 ml. of 20% hydrochloric acid and 20 ml. of water. The mixture was stirred for a time and produced a solution. Examination of it by thin layer chromatography indicated that the demethylation was incomplete. A substantial part of the product was in the form of each of the two possible monomethyl ethers, combined with the desired product, which was identified by thin layer chromatography as substantially identical to the product of Example 1.

EXAMPLE 11

6-hydroxy-2-(4-hydroxyphenyl)-3-[4-(2-piperidinoethoxy)benzoyl]benzo[b]thiophene, hydrochloride A mixture of 1.5 g. of 4-(2-piperidinoethoxy)benzoic acid, hydrochloride, 20 ml. of chlorobenzene, 3 ml. of thionyl chloride and 2 drops of dimethylformamide was stirred at 75°–79° for 2 hours, to prepare the corresponding acid chloride. Vacuum was then applied, and the temperature dropped to 65°. Distillation was continued until the pot temperature was 90°. Twenty ml. of additional chlorobenzene was added, and the mixture was redistilled to a pot temperature of 90°, and was then cooled. To the mixture was added 15 ml. of dichloromethane, 1.35 g. of 6-methoxy-2-(4-methoxyphenyl)-benzo[b]thiophene, 5 g. of aluminum chloride and 15 ml. of additional dichloromethane. The mixture was stirred at 27°–29° for 90 minutes, and then 1.6 ml. of ethanethiol was added. The mixture was stirred with cooling to maintain it at or below 35°. After 30 minutes, the mixture was worked up as described in Example 8 above, except that only 18 ml. of tetrahydrofuran and of water were used, to obtain 2.6 g. of the crude desired product, m.p. 217°, which was found to be substantially identical to the product of Example 1 by nmr and thin layer chromatography.

EXAMPLE 12

6-hydroxy-2-(4-hydroxyphenyl)-3-[4-(2-piperidinoethoxy)benzoyl]benzo[b]thiophene, hydrochloride The process of Example 11 was followed once more, except that 1.8 ml. of ethanethiol was used, and a different work up procedure was applied as follows. The mixture was stirred for 30 minutes after the addition of the ethanethiol, and to it was added 4 ml. of methanol, producing vigorous evolution of gas and a temperature rise, with cooling, to 30°. Six ml. more methanol was added, followed by 5 ml. of 20% hydrochloric acid and 18 ml. of water, while the mixture was held at about 25°. The mixture was stirred for about 30 minutes, and was then filtered. The solids were washed twice with 25 ml. portions of water and twice with 25 ml. portions of diethyl ether. The solids were dried, and found to be 2.55 g. of the crude desired product, m.p. 219° dec., essentially identical to the product of Example 1 by nmr and thin layer chromatography.

EXAMPLE 13

6-hydroxy-2-(4-hydroxyphenyl)-3-[4-(2-hexamethyleneiminoethoxy)benzoyl]benzo[b]thiophene, hydrochloride A 1.6 g. portion of 4-(2-hexamethyleneiminoethoxy)benzoic acid, hydrochloride, was converted to the acid chloride as described in Example 11 and the excess volatiles were removed under vacuum as described in that example. To the acid chloride were added 30 ml. of dichloromethane, 5 g. of aluminum chloride and 1.35 g. of 6-methoxy-2-(4-methoxyphenyl)benzo[b]thiophene. The mixture was stirred for 90 minutes at 27°-29°, and was then cooled. To it was added 1.8 ml. of ethanethiol, and the mixture was stirred for 30 minutes at 32°-34°. The mixture was then cooled, and to it were added 18 ml. of tetrahydrofuran, 5 ml. of 20% hydrochloric acid and 18 ml. of water. The mixture was stirred overnight at ambient temperature, and was then filtered. The solids were washed as described in the example above and vacuum dried to obtain 2.4 g. of the desired product in impure form. The product was crystallized from methanol and vacuum dried to obtain 0.94 g. of the expected product, m.p. 220° dec. Mass spectroscopy showed that the molecular ion had a weight of 487, which is correct for the expected product.

EXAMPLE 14

6-hydroxy-2-(4-hydroxyphenyl)-3-[4-(2-dimethylaminoethoxy)benzoyl]benzo[b]thiophene, hydrochloride A mixture of 1.3 g. of 4-(2-dimethylaminoethoxy)benzoic acid, hydrochloride, 2.5 ml. of thionyl chloride, 20 ml. of chlorobenzene and one drop of dimethylformamide was stirred at 75°-79° for 3 hours to form the acid chloride, and the excess thionyl chloride was distilled off as described above in Example 9. The mixture was then cooled, and to it were added 30 ml. of dichloromethane, 5 g. of aluminum chloride and 1.35 g. of 6-methoxy-2-(4-methoxyphenyl)benzo[b]thiophene. The mixture was then stirred at 27°-29° for about 90 minutes, and was then cooled. To it was added 1.8 ml. of ethanethiol, and the mixture was stirred at 32°-34° for about 30 minutes. It was then worked up as described in Example 13 above to obtain 2.0 g. of the expected product in crude form. The product was purified by crystallizing it from methanol containing 1% water to obtain 1.3 g. of purified product, m.p. 136° dec. Mass spectroscopic analysis of it showed a molecular ion of weight 433, which is correct for the desired product.

EXAMPLE 15

6-hydroxy-2-(4-hydroxyphenyl)-3-[4-(2-pyrrolidinoethoxy)benzoyl]benzo[b]thiophene, hydrochloride To a flask were added 5.71 g. of 4-(2-pyrrolidinoethoxy)benzoic acid, hydrochloride, 10 ml. of thionyl chloride, 4 drops of dimethylformamide and 80 ml. of chlorobenzene. The mixture was stirred at 75°-79° for 2 hours, and was then heated under vacuum until a pot temperature of 90° was reached. Fifty ml. of additional chlorobenzene was added, and the mixture was distilled again in the same manner. It was then allowed to cool, and 120 ml. of dichloromethane, 5.4 g. of 6-methoxy-2-(4-methoxyphenyl)benzo[b]thiophene, and 20 g. of aluminum chloride were added. The mixture was stirred at 27°-29° for about 90 minutes, and was then cooled while 7.4 ml. of ethanethiol was added at about 25°. The mixture was then stirred at 32°-34° for 45 minutes, and was then worked up by the addition of 100 ml. of tetrahydrofuran, 20 ml. of 20% hydrochloric acid, and 100 ml. of water. The mixture was stirred overnight, and was then filtered and the solids were washed with water, and then with a small amount of diethyl ether. The dried product amounted to 9.0 g. of crude expected product, m.p. 202° dec.

The product was recrystallized from methanol and water, then dried under vacuum. Nuclear magnetic resonance analysis of the product then showed that it contained only about 0.5% of methanol, and was substantially identical to the product of Example 7 above.

EXAMPLE 16

Purification of 6-hydroxy-2-(4-hydroxyphenyl)-3-[4-(2-piperidinoethoxy)benzoyl]benzo[b]thiophene, hydrochloride Two hundred g. of crude 6-hydroxy-2-(4-hydroxyphenyl)-3-[4-(2-piperidinoethoxy)benzoyl]benzo[b]thiophene, hydrochloride, typical of the product of Example 11 above, was added to 4400 ml. of methanol and 60 ml. of deionized water in a 5-liter flask. The slurry was heated to reflux, whereupon most of the crude product went into solution. The remaining solid was removed by filtration under vacuum, using a filter aid pad. A distillation head was then attached to the flask, and solvent was distilled off until the volume of the remaining solution was about 1800 ml. The heating mantle was then turned off, and the solution was cooled very slowly overnight, with constant stirring. The crystalline product was then collected by vacuum filtration, and the flask was washed out with filtrate to obtain all of the product. The crystals were washed on the filter with two 100 ml. portions of cold (below 0°) methanol, and the washed product was dried at 60° under vacuum to obtain 140 g. of dried product.

The product was slurried in 3000 ml. of methanol and 42 ml. of water, heated to reflux and cooled very slowly. The product was filtered and dried as above to obtain 121 g. of highly purified product, m.p. 259°-260°.

The compounds are useful for estrogenic, antiestrogenic and antiandrogenic therapy. Accordingly, they are useful in treating pathological conditions of endocrine target organs, which conditions are dependent or partially dependent on an estrogen or on an androgen. Such conditions include mammary cancer, mammary fibrocystic disease, cancer of the prostate, and benign prostatic hypertrophy.

U.S. Pat. No. 4,133,814 teaches that certain of the compounds are also useful as anti-cancer and anti-fertility drugs. The antiestrogenic and antiandrogenic efficacy of a preferred compound prepared by this invention, 6-hydroxy-2-(4-hydroxyphenyl)-3-[4-(2-piperidinoethoxy)benzoyl]benzo[b]thiophene, is explained in further detail in the application of Charles D. Jones entitled Antiestrogenic and Antiandrogenic Benzothiophene, which was filed on the same day as was this application.

The dose of a compound to be administered to a human is rather widely variable. It should be noted that it may be necessary to adjust the dose of a compound when it is administered in the form of a salt, such as a laurate, the salt-forming moiety of which has an appreciable molecular weight. The general range of effective administration rates of the compounds is from about 0.05 mg./kg./day to about 50 mg./kg./day. A preferred rate range is from about 0.1 mg./kg./day to about 10 mg./kg./day, and the most highly preferred range is from about 0.1 mg./kg./day to about 5 mg./kg./day. Of course, it is often practical to administer the daily dose of a compound in portions, at various hours of the day.

The route of administration of the compounds is not critical. The compounds are known to be absorbed from the alimentary tract, and so it is usually preferred to administer a compound orally for reasons of convenience. However, the compounds may equally effectively by administered precutaneously, or as suppositories for absorption by the rectum, if desired in a given instance.

The compounds are usually administered as pharmaceutical compositions. All of the usual types of compositions may be used including tablets, chewable tablets, capsules, solutions, parenteral solutions, troches, suppositories and suspensions. Compositions are formulated to contain a daily dose, or a convenient fraction of a daily dose, in a dosage unit, which may be a single tablet or capsule or a convenient volume of a liquid. In general, compositions contain from about 0.000006% to about 60% of compound, depending on the desired dose and the type of composition to be used.

The activity of the compounds does not depend on the composition in which it is administered or on the concentration of the composition. Thus, the compositions are chosen and formulated solely for convenience and economy.

I claim:

1. A process for preparing a compound of the formula

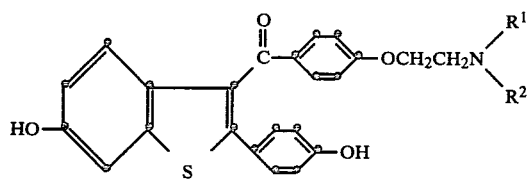

wherein $R^1$ and $R^2$ are independently $C_1$–$C_4$ alkyl, or combine to form $C_4$–$C_6$ polymethylene, —CH$_2$CH(CH$_3$)CH$_2$CH$_2$— or —(CH$_2$)$_2$O(CH$_2$)$_2$—; which process comprises acylating a compound of the formula

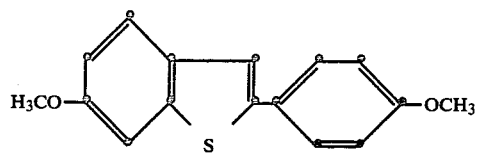

in the presence of aluminum chloride or aluminum bromide with an acylating agent of the formula

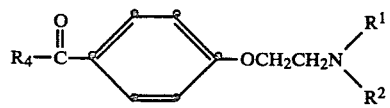

wherein $R^4$ is chloro or bromo; and adding to the reaction mixture a sulfur compound chosen from the group consisting of methionine and compounds of the formula

wherein X is hydrogen or unbranched $C_1$–$C_4$ alkyl, and Y is $C_1$–$C_4$ alkyl or phenyl.

2. A process of claim 1 wherein the product and the acylating agent are compounds wherein $R^1$ and $R^2$ combine to form tetramethylene.

3. A process of claim 1 wherein the product and the acylating agent are compounds wherein $R^1$ and $R^2$ combine to form pentamethylene.

4. A process of claim 1 wherein the product and the acylating agent are compounds wherein $R^1$ and $R^2$ combine to form —CH$_2$CH(CH$_3$)CH$_2$CH$_2$—.

5. A process of any one of claims 1–4 wherein the catalyst is aluminum chloride.

6. A process of any one of claims 1–4 wherein the acylating agent is a compound wherein $R^4$ is chloro.

7. A process of claim 5 wherein the acylating agent is a compound wherein $R^4$ is chloro.

8. A process of any one of claims 1–4 wherein to the reaction mixture is added a $C_1$–$C_4$ alkylthiol.

9. A process of claim 8 wherein the alkylthiol is ethanethiol.

10. A process of claim 5 wherein to the reaction mixture is added a $C_1$–$C_4$ alkylthiol.

11. A process of claim 10 wherein the alkylthiol is ethanethiol.

12. A process of claim 7 wherein to the reaction mixture is added a $C_1$–$C_4$ alkylthiol.

13. A process of claim 12 wherein the alkylthiol is ethanethiol.

* * * * *